US011471010B2

(12) United States Patent
Yoo et al.

(10) Patent No.: US 11,471,010 B2
(45) Date of Patent: Oct. 18, 2022

(54) DRYER STAND AND CONTROL METHOD THEREOF

(71) Applicant: LG ELECTRONICS INC., Seoul (KR)

(72) Inventors: Hyunsun Yoo, Seoul (KR); Jaehung Chun, Seoul (KR); Yousook Eun, Seoul (KR); Joogyeom Kim, Seoul (KR); Sungkyung Kim, Seoul (KR); Myongsun Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 622 days.

(21) Appl. No.: 16/576,407

(22) Filed: Sep. 19, 2019

(65) Prior Publication Data

US 2020/0085257 A1  Mar. 19, 2020

Related U.S. Application Data

(60) Provisional application No. 62/733,478, filed on Sep. 19, 2018.

(30) Foreign Application Priority Data

Feb. 22, 2019 (KR) ........................ 10-2019-0021179
Feb. 22, 2019 (KR) ........................ 10-2019-0021180
Feb. 22, 2019 (KR) ........................ 10-2019-0021183

(51) Int. Cl.
*F24F 3/16* (2021.01)
*A47K 10/48* (2006.01)
(Continued)

(52) U.S. Cl.
CPC .............. *A47K 10/48* (2013.01); *A45D 20/12* (2013.01); *A45D 20/14* (2013.01); *F24F 8/10* (2021.01); *F24F 8/108* (2021.01); *F24F 11/77* (2018.01); *A45D 2020/126* (2013.01); *F24F 8/167* (2021.01); *F24F 2110/65* (2018.01)

(58) Field of Classification Search
CPC ........ A47K 10/48; A45D 20/12; A45D 20/14; A45D 2020/126; F24F 8/10; F24F 8/108; F24F 8/158; F24F 8/167
See application file for complete search history.

(56) References Cited

U.S. PATENT DOCUMENTS

| 4,210,429 A | * | 7/1980 | Golstein | ................. F24F 8/192 |
| | | | | 55/473 |
| 2007/0221061 A1 | * | 9/2007 | Steiner | ...................... F24F 8/10 |
| | | | | 55/467 |

(Continued)

FOREIGN PATENT DOCUMENTS

| CN | 2270133 Y | 12/1997 |
| KR | 20-0369612 Y1 | 12/2004 |
| KR | 10-2018-0043526 A | 4/2018 |

*Primary Examiner* — Jonathan Bradford
(74) *Attorney, Agent, or Firm* — Birch, Stewart, Kolasch & Birch, LLP

(57) ABSTRACT

A dryer stand including a side cover having a through hole through which air is introduced and discharged, a seat provided above the side cover and allowing a dryer to be positioned thereon and an air purifier disposed in an inner space defined by the side cover, wherein the air purifier includes a fan for generating an air flow, and a filter disposed in a flow path of air flowing by the fan to dry a target object.

20 Claims, 12 Drawing Sheets

(51) Int. Cl.
*F24F 8/10* (2021.01)
*A45D 20/12* (2006.01)
*A45D 20/14* (2006.01)
*F24F 8/108* (2021.01)
*F24F 11/77* (2018.01)
*F24F 8/167* (2021.01)
*F24F 110/65* (2018.01)

(56) References Cited

U.S. PATENT DOCUMENTS

2015/0202341 A1* 7/2015 Ediger .................. B01D 53/88
 422/121
2016/0121251 A1* 5/2016 Baek .................. B01D 46/0086
 96/417
2017/0326491 A1 11/2017 Jung

* cited by examiner

DRYER STAND AND CONTROL METHOD THEREOF

CROSS REFERENCE TO RELATED APPLICATIONS

This application claims the priority benefit of U.S. Provisional Application No. 62/733,478, filed on Sep. 19, 2018, Korean Patent Application No. 10-2019-0021179, filed on Feb. 22, 2019, Korean Patent Application No. 10-2019-0021180, filed on Feb. 22, 2019, and Korean Patent Application No. 10-2019-0021183, filed on Feb. 22, 2019, the entire disclosures of all of which are hereby expressly incorporated by reference into the present application.

BACKGROUND OF THE DISCLOSURE

Field of the Disclosure

The present disclosure relates to a dryer stand on which a dryer for drying a predetermined target object is mounted and a control method of the dryer stand, and more particularly to a dryer stand having an air purifying device and a control method of the dryer stand.

Description of the Related Art

When a dryer is used to dry a human body, a user usually grips the dryer and performs a drying operation while moving the dryer with an air outlet of the dryer directed toward a target part to be dried.

In particular, if a drying target is an infant or a pet, the drying operation needs to be performed with a low heating temperature by considering that skin of the infant or the pet is sensitive to high temperature. In addition, in this case, the whole body needs to be dried and thus it takes a long time to complete the drying operation. Therefore, if the user performs the drying operation while gripping the dryer, it may cause inconvenience.

Additionally, attentions are growing for purification of indoor air. In order to purify air in an indoor space which is separated into a living room, a room, etc., it is necessary to provide a plurality of air purifiers.

In addition, the elderly people accounts for an increasing part of population due to development of medical technologies. Aging of human body leads to accumulation of nonenal in pores, which causes unique odor of the elderly people. In addition, more and more households raise pet animals, and the pet animals can have more hair compared to humans and be difficult to wash frequently, and thus causes unpleasant odor. Therefore, it is necessary to remove harmful substances that cause odor in indoor air.

For this reason, a dryer including an air purifying device has been disclosed, but the dryer has a drawback in that the dryer can purify air only in use.

In addition, in the case of purifying air using the dryer, air purification efficiency is low and the air that is blowing causes huge noise.

RELATED ART DOCUMENTS

Patent Documents

Related Art 1: Korean Patent Application Publication No. 10-2015-0031643.

Related Art 2: Korean Utility Model Registration Notification No. 20-0369612.

SUMMARY OF THE DISCLOSURE

An object of the present disclosure is to provide a dryer stand capable of drying a drying target object without gripping a dryer for manipulation of the dryer. That is, the dryer stand can automatically manipulate the dryer to dry a target object, without requiring manual manipulation of the dryer.

Another object of the present disclosure is to provide a dryer stand capable of purifying indoor air, regardless of use of the dryer.

Yet another object of the present disclosure is to provide a dryer stand capable of minimizing an occupied volume in an indoor space and purifying indoor air efficiently.

Yet another object of the present disclosure is to provide a dryer stand capable of purifying indoor air by removing harmful substances that causes unique odor of animals, people, or any other type of odor.

Objects of the present disclosure are not limited to the aforementioned objects, and other objects not mentioned herein will be clearly understood from the following description by those skilled in the art to which the inventive concept pertains.

In order to achieve the aforementioned objects, a dryer stand according to the present disclosure includes a side cover forming a side outer appearance, a seating unit (or seat) receiving dryer thereon, and an air purifying device.

The dryer stand further includes a base disposed to be spaced apart from the seating unit in a downward direction.

The side cover forms a side outer appearance between the base and the seating unit. A through hole through air is introduced and discharged is formed in the side cover.

The side cover may include a front cover forming an outer appearance of the front part, and a rear cover forming an outer appearance of the rear part. The through hole may be formed in the rear cover.

The air purifying device is disposed in the indoor space defined by the side cover. The air purifying device purifies external air by introducing the external air into the inner space, and discharges the purified air to an outside.

The air purifying device includes a blower fan for generating an air flow, and a filter disposed in a flow path of air flowing by the blower fan.

The blower fan may include: an air introduction fan disposed in a lower portion of the inner space and directed toward an upper side; and an air discharge fan disposed above the air introduction fan and directed toward the side cover. The air introduction fan may introduce the external air and send the air to an upper side.

The blower fan may include an air discharge fan disposed above the air introduction fan and directed toward the side cover. The air discharge fan may discharge the air, having passed through the filter, to the outside.

The filter may be disposed between the air introduction fan and the air discharge fan. The filter may include a first surface through which air is introduced, and a second surface through which the air is discharged. The first surface may be disposed to be directed toward the air introduction fan, and the second surface may be disposed to be directed toward the air discharge fan.

The filter may be disposed to be tilted further toward a central portion of the inner space in an upward direction.

The dryer stand may include a stem supporting the seating unit. The air purifying device may be installed at the stem.

The stem may include a vertical plate that extends in the inner space in an upward-downward direction and partitions the inner space into a front part, which is located in a direction in which the dryer discharges drying air, and a rear part, which is opposite to the front part. The stem may further include a lower plate disposed above the base. The stem may further include a rear extension portion extending rearward from an upper side of the vertical plate. The stem may further include a partition wall protruding rearward from the vertical plate and partitioning the rear part in the upward-downward direction.

The vertical plate may extend in the inner space in the upward-downward direction. The vertical plate may extend upward from the lower plate.

The air purifying device may be disposed in the rear part.

The blower fan may include an air introduction fan disposed on the lower plate. The air introduction fan may be directed toward an upper side.

The blower fan may include an air discharge fan disposed above the air introduction fan. The air discharge fan may be directed toward the side cover. The air discharge fan may be directed toward the rear cover. The air discharge fan may be directed toward the through hole.

The air introduction fan may be installed at the lower plate to be directed toward the filter and the air discharge fan, and the air discharge fan may be installed at the vertical plate to be directed toward the rear cover.

A hole may be formed in the partition wall to surround the air introduction fan.

The rear cover may come into contact with left and right side surfaces of the vertical plate. The rear cover may come into contact with an outer circumferential surface of the lower plate. The rear cover may come into contact with an outer circumferential surface of the rear extension portion.

The outer circumferential surface of the partition wall may be formed in a shape corresponding to a portion of an inner surface of the rear cover which opposes the outer circumferential surface of the partition wall, and the rear cover may be disposed to come into contact with the outer circumferential surface of the partition wall.

An upper side of the filter may be supported by the vertical plate, and a lower side of the filter may be supported by the partition wall. The filter may be disposed to become far away from the vertical plate in a downward direction.

The stem may include: an upper supporting piece disposed above the partition wall and protruding rearward from the vertical plate; and a lower supporting piece disposed behind the upper supporting piece and protruding upward from the partition wall.

The filter may be detachably coupled to the upper supporting piece and the lower supporting piece.

The side cover may be formed, of which a height defined in an upward-downward direction is longer than a width defined in a direction vertical to the height.

The through hole may be formed in plural in the side cover along the upward-downward direction.

The filter may include a photocatalyst filter for decomposing harmful substances by photochemical reaction.

The air purifying device may further include a light emitting module for activating the photocatalyst filter.

The light emitting module may be supported by the vertical plate.

The photocatalyst filter may be disposed to become far away from the light emitting module in a downward direction.

The dryer stand may further include: a contamination sensor configured to sense a contamination value of air introduced into the inner space; and a controller configured to control operation of the air purifying device.

The blower fan may include: a motor of which a rotational speed is variable; and a rotational blade rotated by the motor.

The controller may be configured to control that the larger the sensed contamination value, the faster the motor. That is, the controller may be configured to control the speed of the motor of the blower fan in relation to a sensed contamination value, such that an increase in contamination would result in an increase in speed of the motor of the blower fan.

The controller may be configured to: when the sensed contamination value of the contamination sensor is smaller than a preset reference contamination value, operate the air introduction fan and stop the air discharge fan; and, when the sensed contamination value of the contamination sensor is equal to or greater than the preset reference contamination value, operate the air introduction fan and the air discharge fan.

The controller may be configured to: control that the larger the sensed contamination value, the faster the air introduction fan rotates; when the sensed contamination value of the contamination sensor is smaller than the reference contamination value, stop operation of the air discharge fan; and, when the sensed contamination value of the contamination sensor is equal to or greater than the reference contamination value, control that the larger the sensed contamination value the faster the air discharge fan rotates.

The contamination sensor may be disposed in the lower portion of the inner space. The contamination sensor may be disposed on the lower plate.

A control method of a dryer stand according to the present disclosure includes: turning on a light emitting module for activating a photocatalyst filter; sensing a contamination value of air introduced from an outside by an air introduction fan; and, based on the sensed contamination value, operating the air introduction fan and an air discharge fan that discharges air, having passed through the photocatalyst filter, to the outside.

The operating of the air introduction fan and the air discharging fan may include determining whether the sensed contamination value is smaller than a preset reference contamination value.

The operating of the air introduction fan and the air discharging fan may include, when the sensed contamination value is smaller than a preset reference contamination value, operating the air introduction fan and stopping the discharge fan.

The operating of the air introduction fan and the air discharging fan may include, when the sensed contamination value is equal to or greater than a preset reference contamination value, operating the air introduction fan and the air discharge fan.

Other details of embodiments are included in the following detailed description and accompanying drawings.

The dryer stand and the method thereof according to the present disclosure have one or more effects as below.

First, as the dryer stand includes a seating unit on which the dry is seated, it is possible to dry a drying target object without gripping the dryer to manipulate, and reduce a user's fatigue even though it takes a long time to perform a drying operation.

Second, as the dryer stand includes the air purifying device, it is possible to purify indoor space, regardless of use of the dryer.

Third, the seating unit on which the dryer is seated may be provided at a predetermined height for convenience of use. As the air introduction fan is disposed in a lower side, external air may be introduced and sent to an upper side. The air discharge fan is disposed above the air introduction fan, and the filter is disposed between the air introduction fan and the air discharge fan and tilted toward a central portion of the inner space. Accordingly, it is possible to efficiently purify indoor air while minimizing an occupied volume in an indoor space.

Fourth, as the photocatalyst filter for decomposing harmful substances by photochemical reaction and the light emitting module for activating the photocatalyst filter are included, harmful substances causing unique odor, including of pet animals (or animals), people, or any other type of odor. In addition, before a determination as to a contamination value is made, the light emitting module is turned off and thereby the photocatalyst filter is activated, thereby performing air purification more efficiently.

Effects of the present disclosure are not limited to the aforementioned effects, and other effects of the present disclosure which are not mentioned above will become apparent to those having ordinary skill in the art from the claims.

DESCRIPTION OF EXEMPLARY EMBODIMENTS

Figure 1:
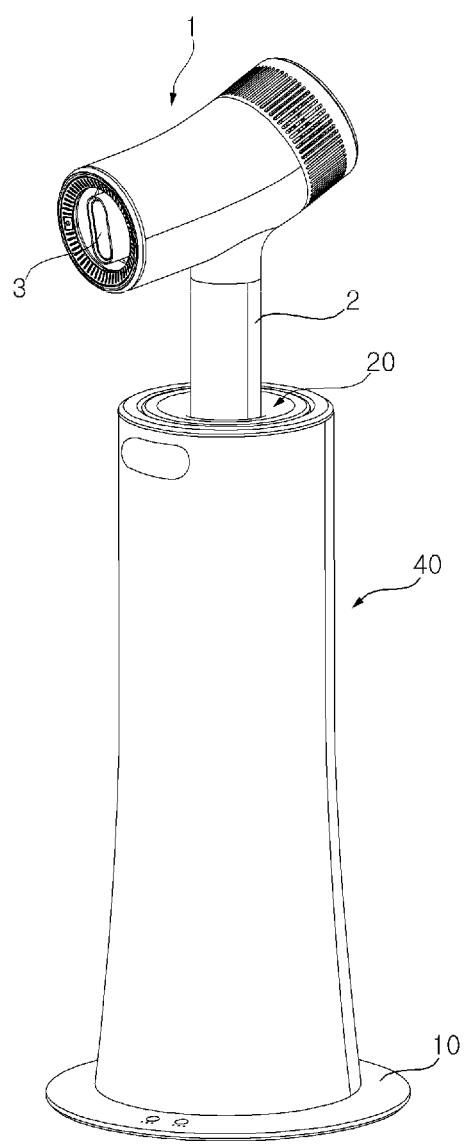
FIG. 1 is a perspective view showing a state in which a dryer is mounted to a dryer stand according to an embodiment of the present disclosure.
Figure 2:
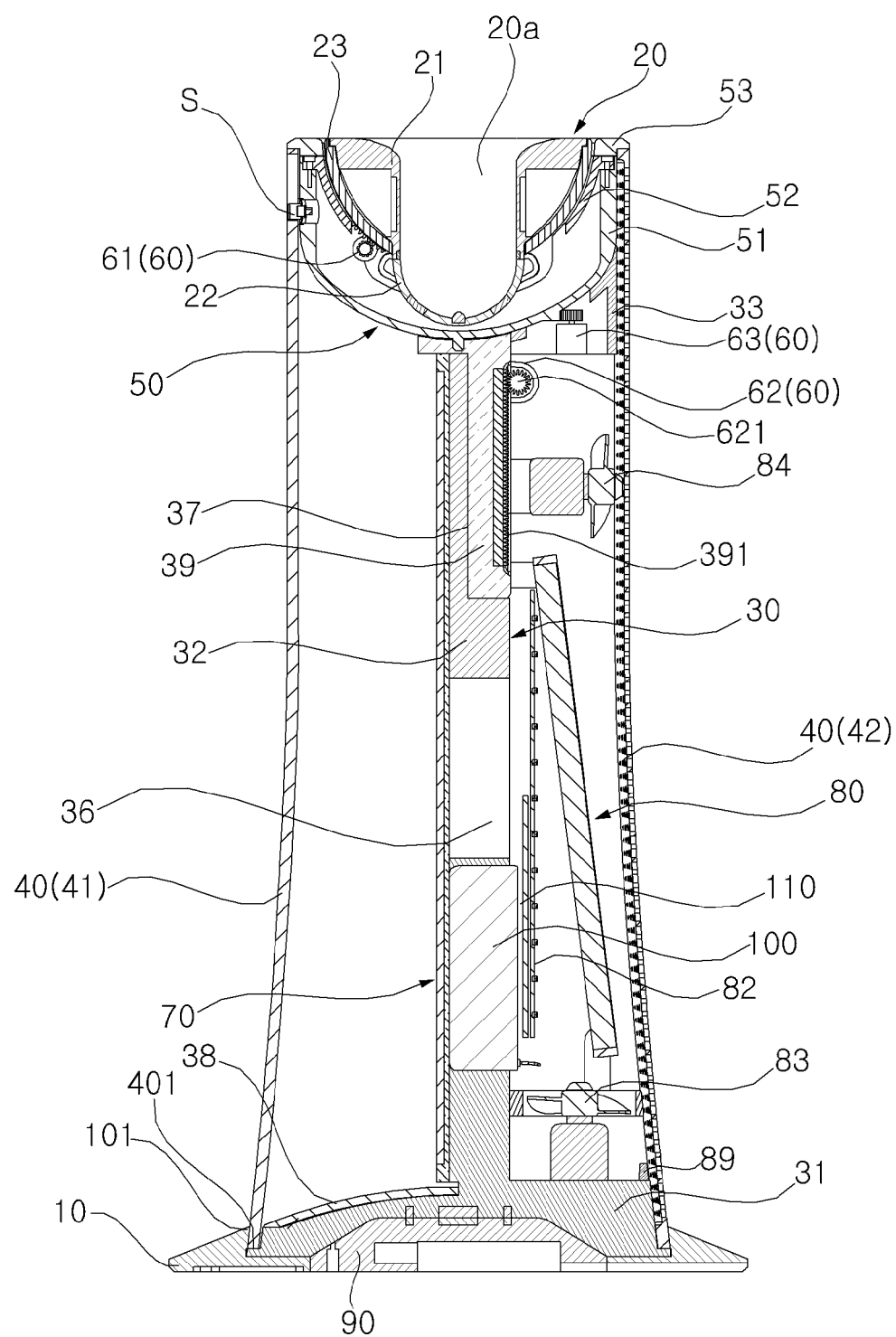
FIG. 2 is a sectional view showing a state in which a dryer stand according to the present disclosure and a docking station are coupled to each other.

Referring to FIGS. 1 and 2, a dryer stand according to an embodiment of the present disclosure includes a base 10 disposed at a lower portion of the dryer stand, a side cover 40 forming a side outer experience of the dryer stand, a seating unit 20 and 50 where the dryer is seated, and an air purifying device 80 (or air purifier) for purifying air inside the dryer stand.

The seating unit 20 and 50 may include a receptacle 20 to which the dryer 1 is detachably mounted, and a supporter 50 movably supporting the receptacle 20. The supporter 50 may movably support the receptacle 20 in between a stem 30 described in the following.

The "movement" described above is interpreted as including tilting rotation indicating rotation in a forward-backward direction, a leftward and rightward rotation indicating rotation in a leftward-rightward direction, or a straight forward movement indicating movement in an upward-backward direction or in a vertical direction.

The base 10 is spaced apart from the seating unit 20 and 50 in a downward direction.

The side cover 40 forms a side outer appearance to thereby define an inner space distinguishable from an outside of the dryer stand (an indoor space where the dryer stand is placed). In the side cover 40, a through hole 421 through which air is introduced and discharged is formed. The side cover 40 may form a side outer appearance between the base 10 and the seating unit 20 and 50

The air purifying device 80 is disposed in the inner space defined by the side cover 40. The air purifying device 80 includes blower fans 83 and 84 for generating an air flow, and a filter 81 installed in a flow path of air flowing by the blower fan 83 and 84. However, the air purifying device 80 can include a single blower fan 83. The filter 81 includes a photocatalyst filter 81 that decompose harmful substances by photochemical reaction. The following description about the filter 81 may apply to the photocatalyst filter 81.

The air purifying device 80 may include a light emitting module 82 that activates the photocatalyst filter.

The dryer stand according to an embodiment of the present disclosure may include the stem 30 that is inserted in between the base 10 and the seating unit 20 and 50 in the upward and downward direction to support the receptacle 20 so that the receptacle 20 can be positioned at a predetermined height in the upward direction from the base 10.

In addition, the dryer stand may include a motor 60 that moves the seating unit 20 and 50.

In addition, the air purifier 80 of the dryer stand may include one or more of the blower fans 83 and 84 that generate an air flow, and the blower fans 83 and 84 may include an air introduction fan 83 for introducing external air and an air discharging fan 84 for discharging air having passed through the photocatalyst filter 81 to the outside.

In addition, the dryer stand according to an embodiment of the present disclosure may include a drying object sensing apparatus S for sensing a size or a location of an object to by dried, and a controller 110 for controlling operation of the motor 60 according to the size or location of the drying object sensed by the drying object sensing apparatus. The controller 110 may control an overall operation of the dryer stand, including the motor 60 for moving the seating unit 20, 50 and the air purifying device 80.

In addition, the dryer stand according to an embodiment of the present disclosure may include a lighting device 70, and the dryer stand includes a power supply for supplying external power to the dryer stand when the dryer stand is placed on a docking station 90 that provides the external power.

Hereinafter, constituent elements of the dryer stand will be described in more detail.

Figure 3:
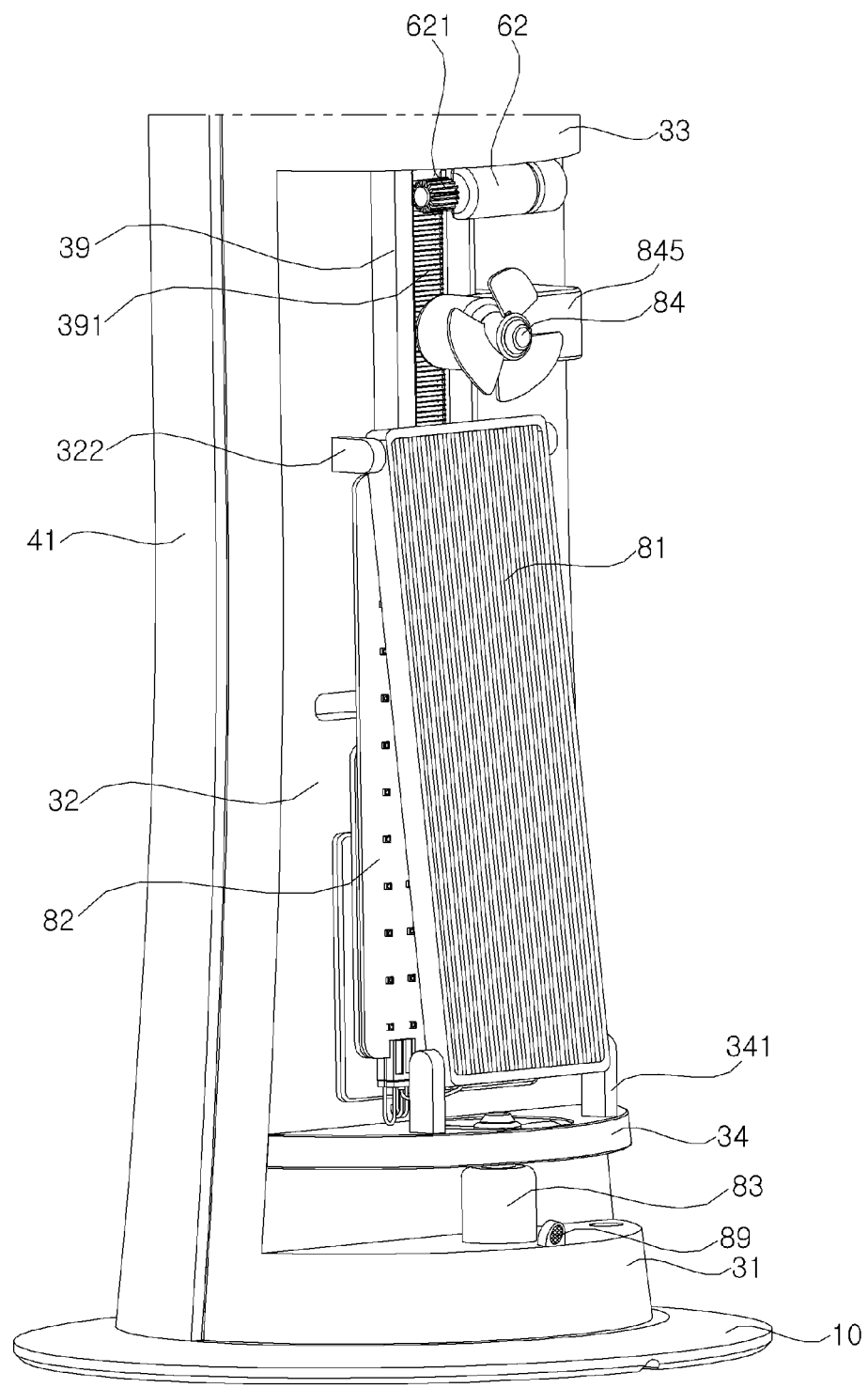
FIG. 3 is a perspective view showing an air purifying device installed at a rear part of an inner space of a dryer stand according to an embodiment of the present disclosure.
Figure 4:
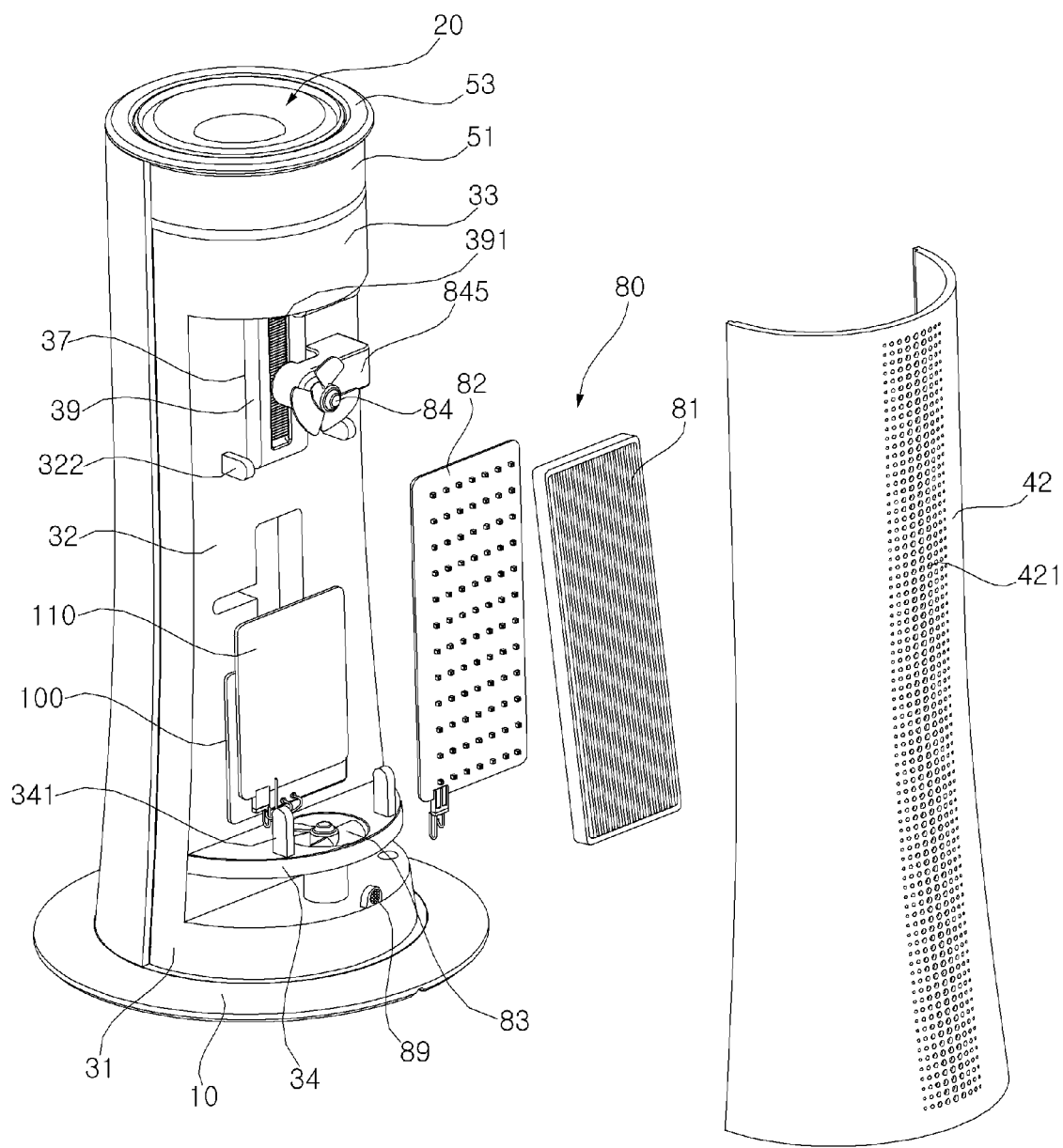
FIG. 4 is a rear exploded perspective view of a dryer stand according to an embodiment of the present disclosure.

Referring to FIGS. 2, 3, and 4, the stem 30 may support the seating unit 20 and 50 and the air purifier 80 may be installed at the stem 30. The stem 30 may include a lower plate 31 engaged with a lower end 401 of the side cover 40, a vertical plate 32 extending upwardly from the lower plate 31, and a rear extension portion 33 extending rearwardly from an upper end of the vertical plate 32.

The lower plate 31 may be disposed above the base 10 and coupled to the base 10 by a fastening means such as a set screw or the like. A hollow portion 12 may be formed at a center of a bottom surface of the base 10. Thus, the bottom surface of the base 10 may be formed in a ring shape, and thus, when the dryer stand is viewed from below, a bottom surface of the lower plate 31 may be exposed. A reflection plate 38 may be positioned on the top side of the front of the lower plate 31.

When the dryer stand is mounted to the docking station 90, an upper space of the docking station 90 may protrude upwardly through the hollow portion 12 of the base 10 and the docket station may come into contact with the bottom surface of the lower plate 31. The bottom surface of the lower plate 31 and the upper surface of the docking station 90 may respectively have terminals that electrically connect the lower plate 31 and the docking station 90 to each other.

The air introduction fan 83 described below may be installed on a rear side of an upper surface of the lower plate 31, as illustrated in FIGS. 3 and 4. An outer circumferential surface of the lower plate 31 may be formed in a shape corresponding to an inner circumferential surface of a lower end of the side cover 40.

The vertical plate 32 may extend upwardly from the lower plate 31 and partition the inner space of the dryer stand into a front part and a rear part. The front part corresponds to a direction in which the dryer 1 seated in the seating unit 20 and 50 discharges air (a direction in which an air outlet 3 is disposed), and the rear part corresponds to a direction opposite to the front part. On the vertical plate 32, the photocatalyst filter 81 and the light emitting module 82 may be installed.

Below the vertical plate 32, a partition wall 34 protruding rearward may be formed. The partition wall 34 may partition the rear part of the inner space of the dryer stand into a space where air is introduced and a space where air is purified and discharged. A hole may be formed in the partition wall 34 and surround the air introduction fan 83. That is, the partition wall 34 may function as a housing for the air introduction fan 83.

An outer circumferential surface of the partition wall 34 may be formed in a shape corresponding to a portion of the inner surface of a rear cover 42, which opposes the outer circumferential surface of the partition wall 34. In addition, the outer circumferential surface of the lower plate 31 may be formed in a shape corresponding to the rear cover 42. As the rear cover 42 may be disposed to come into contact with the lower plate 31 and the outer circumferential surface of the partition wall 34, external air can be efficiently introduced and sent when the air introduction fan 83 is operated.

The lighting device 70 may be installed at a front surface of the vertical plate 32. The air discharge fan 84, the filter 81, and the light emitting module 82 may be installed at a rear surface of the vertical plate 32. In addition, a hollow portion 35 may be formed at a lower central portion of the vertical plate 32 and a battery 100 may be installed at the hollow portion 35. A hole 36 allowing an electric wire to pass there-through may be formed above the battery 100, and the controller 110 may be disposed at rear of the battery 100.

The controller 110 may control operation and a rotational speed of the blower fan 83 and 84 according to a sensed value of a contamination sensor 89 described below.

In addition, a long groove 37 may be formed in the upward-downward direction at a rear of the upper side of the vertical plate 32 and at least a part of the vertical rod 39 may be inserted into the long groove 37 so that the vertical rod 39 can be moved upwardly and downwardly.

Left and right side ends of the vertical plate 32 may be formed in a shape corresponding to left and right side ends of a front cover 41 and a rear cover 42, such that the left and right side ends of the vertical plate 32 are disposed to be in contact with the side cover 40.

The rear extension portion 33 may be extended rearward from the upper end of the vertical plate 32 and then bent downward. The upper surface of the rear extension portion 33 may be formed in a shape corresponding to a lower surface of a supporter main body 51 and may be disposed to surround a rear side of a lower surface of the seating unit 20 and 50.

An arc-shaped hole having a width greater than a width of a gear teeth 512 formed in the supporter main body 51 may be formed in the upper surface of the rear extension portion 33. Through the arc-shaped hole, a pinion 631 fixed to a rotation motor 63 and the gear teeth 512 may be engaged. When the seating unit 20 and 50 is moved, the rotation motor 63 may pass through the arc-shaped hole.

An outer circumferential surface of the rear extension portion 33 may be formed in a shape corresponding to the rear cover 42, and the rear cover 42 may be disposed to come into contact with the rear extension portion 33.

Referring to FIG. 2, the dryer stand includes the vertical rod 39 disposed below the seating unit 20 and 50. The vertical rod 39 may be coupled to the vertical plate 32 to support the seating unit 20 and 50 so that the seating unit 20 and 50 can move upward and downward.

A rack gear 391 is formed in a rear surface of the vertical rod 39. As the rack gear 391 is gear-engaged with the pinion gear 621 fixed to a rotation shaft of an elevation motor 62, the rotation rod 39 is elevated upon forward and backward rotation of the elevation motor 62.

The supporter 50 may be disposed above the vertical rod 39, and the receptacle 20 to which the dryer 1 is mounted may be movably accommodated in the supporter 50.

Referring to FIGS. 2, 6, 7, and 8, the seating unit 20 and 50 may include the receptacle 20 to which the dryer 1 is detachably mounted, and the supporter 40 movably supporting the receptacle 20.

The supporter 50 may include the supporter main body 51 rotatably connected to the upper surface of the vertical rod 39, and a guide supporter 52 fixed to an upper surface of the supporter main body 51 by a set screw 514 and accommodated in the supporter main body 51.

Figure 7:
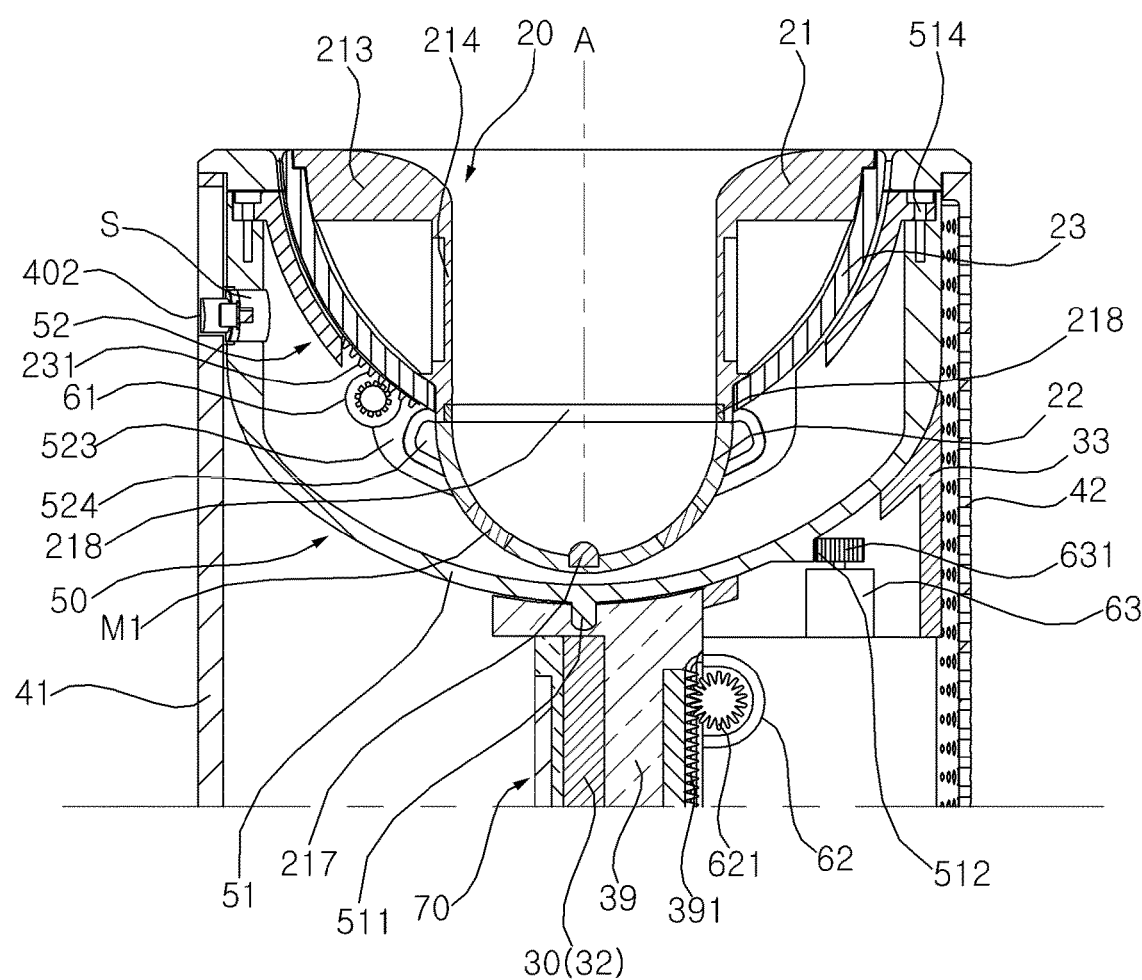
FIG. 7 is a cross-sectional view of an upper side of a dryer stand according to an embodiment of the present disclosure.
Figure 8:
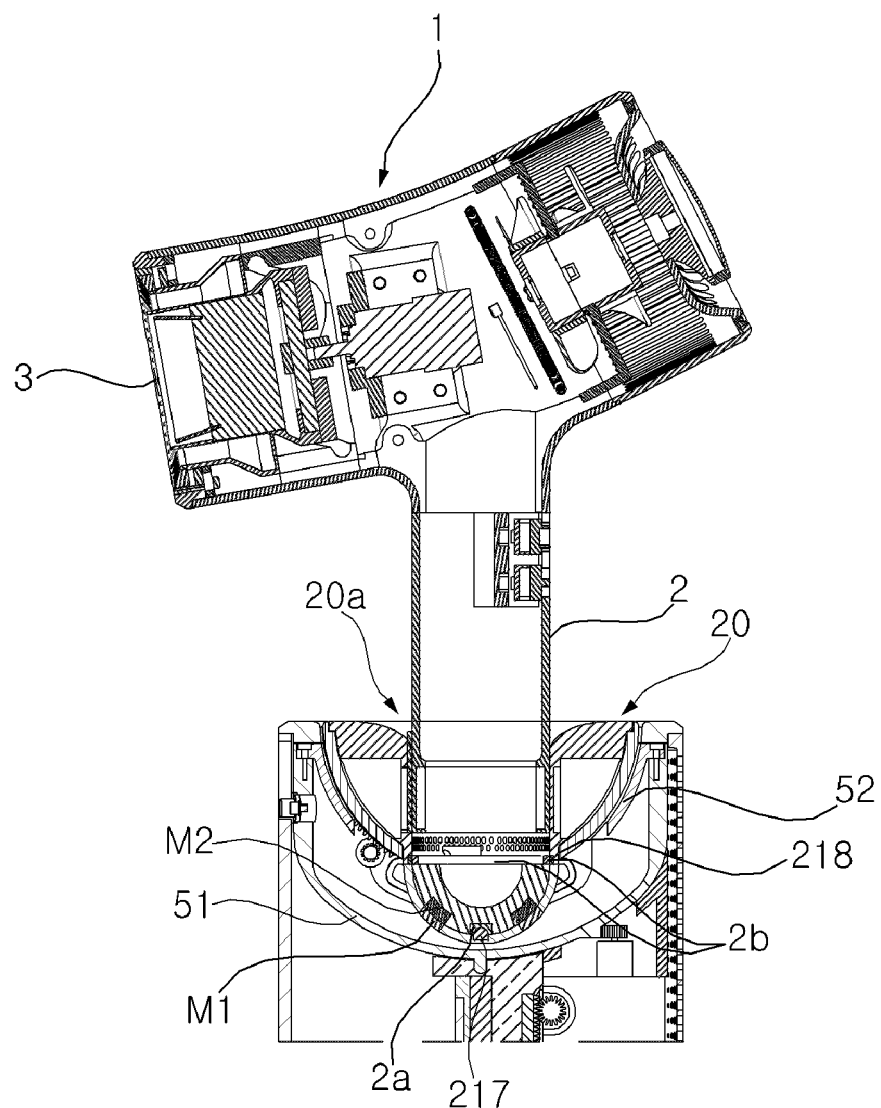
FIG. 8 is a cross-sectional view of an upper side, which shows a state in which a dryer is mounted to a dryer stand according to an embodiment of the present disclosure.

As shown in FIG. 7, the supporter main body 51 may be formed to have an open upper side and a lower side, which is approximately in a hemispherical shape. A protrusion 511 may be formed at a bottom surface of the supporter main body 51, and the protrusion 511 may be rotatably inserted into a groove formed in the upper surface of the vertical rod 39.

The gear teeth 512 is formed to extend in an arc shape in a side surface direction of an outer circumferential surface of the lower side of the supporter main body 51. The gear teeth 512 may be gear-engaged with the pinion 631 fixed to the rotation shaft of the rotation motor 63. Accordingly, the supporter main body 51 and the guide supporter 52 fixed to the supporter main body 51 may be rotated leftward and rightward about a vertical axis A when the rotation motor 63 is rotated forward and backward.

Accordingly, the supporter 51 and 52 may be elevated upward and downward when the elevation motor 62 is operated, and the supporter 51 and 52 may be rotated leftward and rightward when the rotation motor 63 is operated.

The guide supporter 52 may include a horn-shaped guide main body 521, of which a lower central portion 522 is open and of which an inner surface forms an arch shape in the upward-downward direction, and a pair of guide rails 523 which protrudes from both sides of the guide main body 521 and in which an arc-shaped guide groove 524 is formed in the forward-downward direction. A buffer rail 525 performing a buffer function and reducing friction may be inserted into the guide rail 523.

The receptacle 20 to which the dryer 1 is mounted may include a tub 21 and 22, forming a groove 20a into which a grip 2 of the dryer 1 is inserted. The tub 21 and 22 may include an upper tub 21 and a lower tub 22. A tub cover 23 covered on a periphery of the upper cover 21 may be included. The lower tub 22 may include an aperture 226 that forms a portion of the groove 20a of the tub 21, 22. That is, the groove 20a of the tub 21, 22 may also include the aperture 226 of the lower tub 22. A portion 214 positioned between the concave part 213 and the groove 20a has a smaller thickness than other portions due to the concave part 213.

The tub 21 may include a tub main body 211 which is in a downwardly-narrowed and approximate semispherical shape, and a lower protruding portion 212 extending downward from the tub main body 211. A concave portion 213 inwardly recessed may be formed in at least one side surface of the tube main body 211. The upper tub 21 may include an aperture 216 that forms a portion of the groove 20a of the tub 21, 22. That is, the groove 20a of the tub 21, 22 includes an aperture 216 of the upper tub 21.

Due to the concave portion 213, a portion between the concave 213 and the groove 20a may have a thickness relatively thin compared to other portions. Therefore, during operation of the dryer 1, heat generated inside the grip 2 of the dryer 1 inserted into the groove 20a may be dissipated through the concave portion 213.

A groove 225 may be formed in an upper surface of the lower tub 22. A protrusion 215 formed in a lower surface of the upper tube 21 is inserted into the groove 225 and thereby the lower tub 22 may be integrally coupled to the upper tub 21. A protruding piece 224 may be fastened to both side surfaces of the lower tub 22 by a set screw 227, and the protruding piece 224 may be movably inserted into a guide groove 524 formed in the guide rail 523 of the guide supporter 52. In order to guide the rotation and tilting of the receptacle 20 in the front and rear direction more stably, a protruded part 232 is formed at the outer side of the tub cover 23, and a groove 526 into which the protruded part 232 is inserted and guide may be formed in the inner side of the guide body 521.

Additionally, the tub cover 23 may be formed in an approximate downwardly-narrowed hemispherical shape. The tub cover 23 may be disposed to surround a periphery of the tub main body 211 of the upper tub 21 and may be integrally coupled to the upper tub 21.

A gear teeth 231 extending in an arc shape in the upward-downward direction may be formed in an outer surface of the tub cover 23. A pinion 611 fixed to the rotation shaft of the tilting motor 61 may be gear-engaged with the gear teeth 231 of the tube cover 23. Accordingly, when the tilting motor 61 is rotated in the forward-backward direction, the receptacle 20, 21, 22, and 23 may be tilted in the forward-backward direction as the protruding piece 224 moves while being guided by the guide groove 524 of the guide supporter 52.

Thus, the receptacle 20, to which the dryer 1 is mounted, may be tilted in the forward-downward direction upon operation of the tilting motor 61. The receptacle 20 may be elevated in the upward-downward direction upon operation of the elevation motor 62. The receptacle 20 may be rotated in the leftward-rightward direction upon operation of the rotation motor 63. Accordingly, an orientation of the air outlet 2 of the dryer 1 may be changed variously.

Additionally, a ring-shaped upper cover 53 may cover the upper side of the supporter 50.

In addition, an image photographing apparatus for sensing a size and a location of a drying object or a drying object sensing apparatus S, such as a proximity sensor, may be mounted to a front surface of the supporter main body 51.

Figure 5:
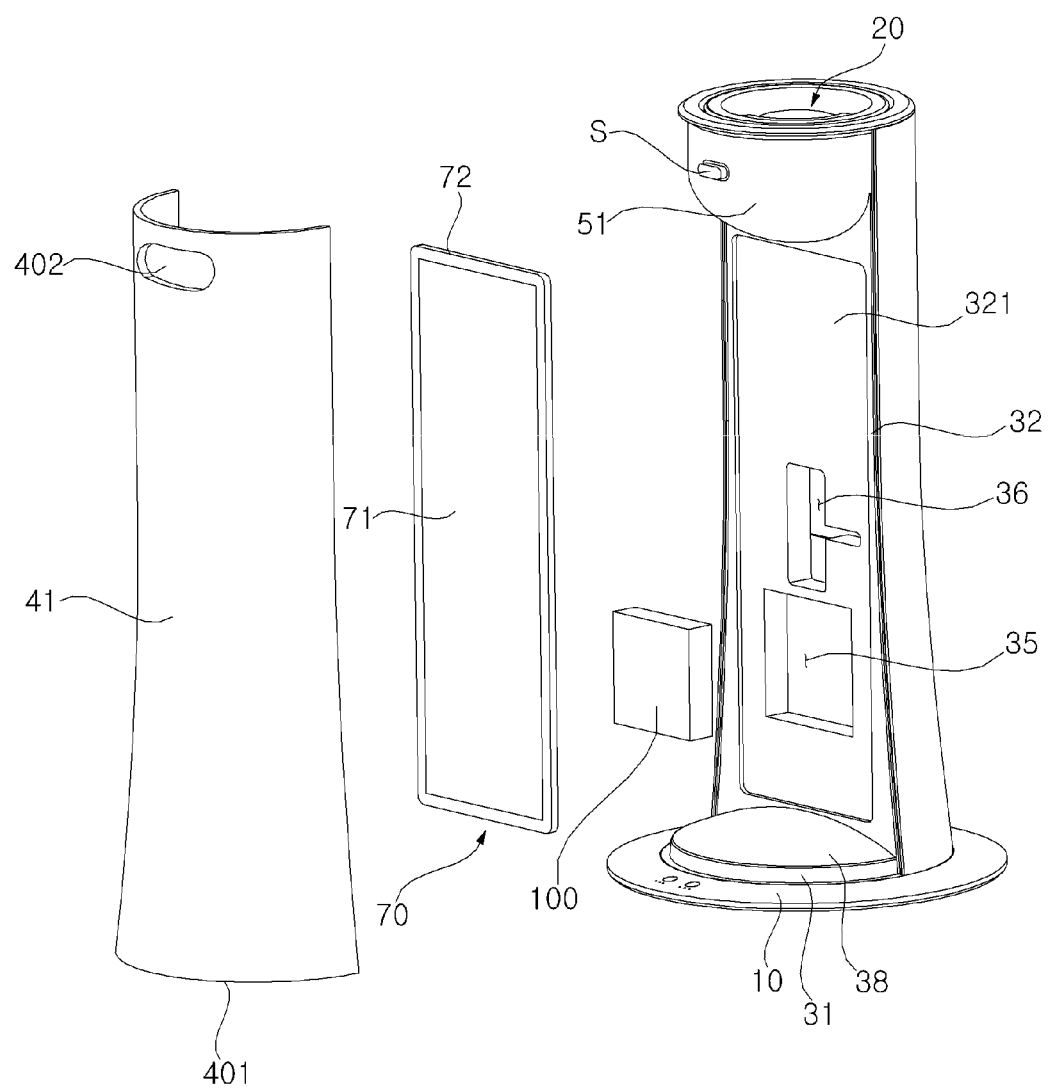
FIG. 5 is a front exploded perspective view of a dryer stand according to an embodiment of the present disclosure.

Referring to FIGS. 4 and 5, the side cover 40 forming a side outer appearance of the dryer stand may include the front cover 41 and the rear cover 42. The side cover 40 may include the front cover 41, which forms an outer appearance of a front side toward which the dryer 1 seated in the seating unit 20 and 50 discharges air (a direction in which the air outlet 3 is disposed), and the rear cover 42, which forms an outer appearance of a rear side opposite to the front side.

The front cover 41 is disposed at a front of the lighting device 70, and the rear cover 42 is disposed at a rear of the air purifying device 80. The side cover 40 may be installed as the side cover 40 is fitted into a ring-shaped groove 101 that is formed by the base 10 and the lower plate 31 (see FIG. 2).

The front cover 41 may be formed of a transparent or semi-transparent material so that light emitted from the lighting device 70 is radiated to the outside. The rear cover 42 may be disposed at a rear of the front cover 41 and coupled to the front cover 41.

A plurality of through holes 421 may be formed in the rear cover 42. When the air introduction fan 83 and/or the air discharge fan 84 is operated, air may be introduced into the rear cover 42 through the plurality of through holes 421 and may be then discharged to the outside through the plurality of through holes 421 by passing through the filter 81.

The plurality of through holes 421 may be formed at a height between at least the partition wall 34 of the rear cover 42 and the lower plate 31, and may be formed at a height at which the air discharge fan 84 is disposed. The plurality of through holes 421 may be formed in plural from a portion of the rear cover 42 in contact with the lower plate 31 to a position higher than the air discharge fan 84 along the upward-downward direction.

As the rear cover 42 is disposed to come into contact with the left and right side ends of the vertical plate 32, a rear outer circumferential surface of the lower plate 31, the partition wall 34, and an outer circumferential surface of the rear extension portion 33, the rear cover 42 may tightly cover the rear part of the inner space where the air purifying device 80 is installed. Accordingly, air may be introduced and discharged through the plurality of through holes 421 formed in the rear cover 42, and thereby air purification may be performed efficiently.

Additionally, the upper side of the front cover 41 and the rear cover 42 is disposed to surround the supporter main body 51 so that the supporter main body 51 can move upward and downward. The ring-shaped upper cover 52 coupled to the upper side of the supporter main body 51 may be movably disposed on the upper surfaces of the front cover 41 and the rear cover 42.

Referring to FIG. 5, the lighting device 70 may include a light emitting panel 71 and a lighting frame 72. The light emitting panel 71 may be formed as a Light Emitting Diode (LED) plate in which a plurality of LEDs is embedded.

As a concave portion 321 recessed rearward may be formed in the front surface of the vertical plate 32, the lighting frame 72 is inserted into the concave portion 321 and thereby the lighting device 70 may be detachably seated in the concave portion 321. The concave portion 321 may be recessed from the front surface of the vertical plate 32 to be in a shape corresponding to a shape of the lighting device 70. A reflection plate 38 from which light radiated by the light-emitting panel 71 is reflected may be provided on the front top surface of the lower plate 31. The back top surface of the lower plate 31 has a horizontal plane. In contrast, the reflection plate 38 is convexly formed upward toward the central part of the lower plate 31. The reflection plate 38 is also formed in a shape corresponding to the shape of front top surface of the lower plate 31. Accordingly, light radiated by the light-emitting panel 71 can be uniformly directed toward the front cover 41.

The light emitting panel 71 may be formed as an Organic Light Emitting Diode (OLED) plate in which an OLED is embedded. Light emitted from the OLED is known as having light spectrum more similar to that of natural light than currently developed other light emitting sources. Therefore, if the light emitting panel 71 is made using an OLED, it helps relieve seasonal affective disorder of a user or an animal (e.g., a pet) due to lack of outdoor activities.

In addition, the OLED generates less blue light. The blue light is defined as a visible light in a low wavelength range of 380 to 500 nm, and has the strongest energy among visible light. The blue light is effective in increasing concentration and but disturbs release of melatonin hormone, thereby causing sleeping disorder, and leads to dry eyes and macular degeneration. Thus, if the light emitting panel 71 is made using an OLED, seasonal affective disorder may be alleviated and sleeping disorder caused by light pollution may be prevented.

The OLED may be made to form a surface and thereby constitute a surface light source and may be able to uniformly emit light into a wide area. Therefore, the OLED gives less glares and does not cast a strong shadow, thereby improving quality of an indoor space.

The OLED may have a thin thickness and may be bendable. Thus, the light emitting panel 71 may be made of the OLED and formed to be curved to thereby come into tight contact with the inner surface of the front cover 41, thereby improving radiation of light emitted from the OLED panel.

A plurality of LEDs and/or OLEDs for radiating lights of different wavelengths is amounted in the lighting device 70. Accordingly, a light preferred by a drying object may be emitted, and a drying degree of a drying target part may be sensed during a drying operation, and a different color may be emitted according to the sensed dry degree.

Referring to FIGS. 2, 3, and 4, the air purifying device 80 includes the blower fans 83 and 84 for generating an air flow, and the filter 81 installed in a flow path of air flowing by the blower fans 83 and 84. The air purifying device 80 may be disposed in the rear part of the inner space. The through hole 421 formed in the rear cover 40 may be formed in the rear cover 42.

Accordingly, an operation for drying an object through the dryer 1, and light therapy for alleviating depressing through the lighting device 70 may be performed at the front of the dryer stand, and air circulation and purification may be performed at the rear of the dryer stand.

The blower fans 83 and 84 may include the air introduction fan 83, which is disposed in a lower side of the inner space defined by the side cover 40, and the discharge fan 84, which is disposed above the air introduction fan 83. Each of the air introduction fan 83 and the air discharge fan 84 may include a rotational blade and a motor. Motors for driving the air introduction fan 83 and the air discharge fan 84 may be motors of which rotational speeds are variable.

The air introduction fan 83 may introduce external air and send the introduced air to the upper side, and the air discharge fan 84 may discharge air, having flown to the upper side by the air introduction fan 83 and then passed through the filter 81, to the outside.

The air introduction fan 83 may be installed at a rear side of an upper surface of the lower plate 31. A motor is disposed on the lower plate 31 so that a rotational blade of the air introduction fan 83 is spaced apart from the lower plate 31, and the rotational blade may be disposed to be directed upward.

In addition, the partition wall 34 may be spaced apart upwardly from the lower plate 31. As a hole is formed in the partition wall 34, the hole may surround the air introduction fan 83 (the rotational blade of the air introduction fan 83). Accordingly, when the air introduction fan 83 is operated, external air is introduced into a space between the partition wall 34 and the lower plate 31 through the through hole 421 formed in the lower side of the rear cover 42, and the introduced air is sent upwardly through the hole surrounding the air introduction fan 83.

The air discharge fan 84 may be disposed at a rear surface of the vertical plate 32 and may be disposed above the air introduction fan 83 and above the filter 81. That is, the air discharge fan 84 may be disposed above the partition wall 34. A motor of the air discharge fan 84 may be disposed to be directed toward the vertical plate 32, and the rotational blade may be disposed to be directed toward the rear cover 42.

As shown in FIG. 4, the air discharge fan 84 may be supported by the air discharge fan support 845 that is coupled to the vertical plate 32. The air discharge fan support 845 may be coupled to the rear surface of the vertical plate 32, extended from the rear surface of the vertical plate 32 toward the rear, and then bent toward a side surface and thereby the air discharge fan 84 may be disposed at the rear of the vertical rod 39. The motor of the air discharge fan 84 may be installed at the air discharge fan support 845, and the rotational blade of the air discharge fan 84 may be disposed to be directed toward the rear cover 42.

The air discharge fan 84 may be spaced apart from the rear of the vertical plate 32 by the air discharge fan support 845, and the vertical rod 39 may be disposed in between the vertical plate 32 and the air discharge fan 84, which are spaced apart from each other.

When both the air introduction fan 83 and the air discharge fan 84 are operated, air introduced by the air introduction fan 83 from the outside and then sent to the upper side passes through the filter 81 quickly and is then discharged to the outside by the air discharge fan 84. Accordingly, if a contamination value of air in the outside of the dryer stand (an indoor space or the like) is high, both the air introduction fan 83 and the air discharge fan 84 may be operated, thereby circulating and purifying air quickly.

When one of both the air introduction fan 83 and the air discharge fan 84 is operated alone, an air flow rate may be decreased and thus a time for the air to stay in the air purifying device 80 may be extended. Accordingly, when a contamination value of external air is low, a time for the air to come into contact with the filter 81 may be increased, thereby decomposing and filtering out a small amount of contaminants existing in the air and reducing noise caused by the blower fan.

In a case where one of both the air introduction fan 83 and the air discharge fan 84 is operated alone, when the air discharge fan 84 is operated alone, air may be discharged to the outside by the air discharge fan 84, pressure in a space where the air purifying device 80 is installed may be reduced, and, in turn, the air may be introduced. In this case, the air may be introduced through a through hole formed above the partition wall 34, and the air may be discharged without passing through the filer.

Additionally, when the air discharge fan 83 is operated alone, air in a space between the partition wall 34 and the lower plate 31 may be sent to the upper side of the partition wall 34, pressure may be reduced, and, in turn, external air may be introduced. In this case, the air may pass through the filter 81, be accumulated in the upper side, and be then discharged to the outside. Accordingly, when the air introduction fan 83 is operated alone, a time for the air to stay in the air purifying device 80 may be extended and introduced air may pass through the filter 81 and be then discharged.

Therefore, when one of both the air introduction fan 83 and the air discharge fan 84 is operated alone, it may be desirable to operate the air introduction fan 83 alone.

The filter 81 may be disposed between the air introduction fan 83 and the air discharge fan 84. The filter 81 may include a first surface through which air is introduced, and a second surface through which the air is discharged. The first surface may be disposed to be directed toward the air introduction fan 83, and the second surface may be disposed to be directed toward the air discharge fan 84.

The filter 81 may be disposed to be tilted toward the center of the inner space in an upward direction. An upper side of the filter 81 may be supported by the vertical plate 32, and a lower side of the filter 81 may be supported by the partition wall 34.

Accordingly, the dryer stand may occupy a small volume and widen an area of the filter 81 which comes into contact with air, thereby enabled to purify the air efficiently.

Additionally, the stem may include an upper supporting piece 322 protruding rearward from the rear of the vertical plate 32, and a lower supporting piece 341 protruding upward from the partition wall 34. The filter 81 may be detachably installed to the upper supporting piece 322 and the lower supporting piece 341. That is, the lower supporting piece 341 extends substantially along a vertical direction, the upper supporting piece 322 extends substantially along a horizontal direction (e.g., a rear direction), and the vertical direction being at least substantially perpendicular to the horizontal direction.

The upper supporting piece 322 may be provided as a pair of supporting pieces spaced apart from each other and may support the upper side of the filter 81. The lower supporting piece 341 may be provided as a pair of supporting pieces spaced apart from each other and may support the lower side of the filter 81. The filter 81 may be fitted into between the pair of the upper supporting pieces 322 and the pair of lower supporting pieces 341, the lower side of the filter 81 is detachably installed in a tilted manner while protruding rearward, compared with the upper side of the filter 81. The light emitting module 82 may be positioned in front of the filter 81, and a spacing between the filter 81 and the light emitting module 82 may increase in the downward direction towards a base 10.

Additionally, the filter 81 may use a photocatalyst filter 81 that can be used for deodorization as well. The photocatalyst filter 81 may decompose harmful substances by photochemical reaction. Arrangement position, structure, and the like of the photocatalyst filter 81 may be identical those of the above-described filter 81.

The photocatalyst filter 81 may be composed of an air-permeable adsorbent substrate, a photocatalyst attached to the air-permeable adsorbent substrate, and a promoter which helps the activation of the photocatalyst.

The air-permeable adsorbent substrate may be formed as a pulp that is wrinkled multiple times so as to make a large area where air passes through and comes into contact. The air-permeable adsorbent substrate may include a porous material so that harmful materials can be adsorbed. The porous material is preferably activated carbon, zeolite, activated alumina, clay molded body, fiber molded body, ceramics, metal, plastic, etc.

The photocatalyst decomposes harmful substances adsorbed to the air-permeable adsorbent substrate by photochemical reaction. The photocatalyst according to the present disclosure is preferably a visible-ray photocatalyst that can apply to visible light rays comes not just from sunlight, but also from a fluorescent lamp and an incandescent lamp. The photocatalyst may include at least one component selected from among Tungsten Oxide ($WO_3$), Titanium Oxide ($TiO_2$), Zinc Oxide (ZnO), Zirconium dioxide ($ZrO_2$), and solid solution consisting of Tungsten Oxide ($WO_3$), Titanium Oxide ($TiO_2$), Zinc Oxide (ZnO), and Zirconium dioxide ($ZrO_2$).

The promoter may include one or more of a metal, an oxide, or a composition selected from platinum (Pt), rhodium (Rh), ruthenium (Ru), palladium (Pd), silver (Ag), copper (Cu), and Zinc (Zn). In the present embodiment, it is preferable that the promoter is platinum (Pt) to maximize activation of a photocatalyst by a visible light.

The air purifying device may include the light emitting module 82 for activating the photocatalyst filter 81, and the light emitting module 82 may be a blue light emitting panel 82. The light emitting module 82 may include a plurality of light emitting bodies, and the plurality of light emitting lights may be blue Light Emitting Diodes (LEDs). The light emitting module 82 may be a blue LED panel including the blue LEDs.

The light emitting module 82 may be installed at a vertical plate, and the light emitting module 82 may be installed between the vertical plate 32 and the photocatalyst filter 81 and in parallel with the vertical plate 32.

Figure 9:
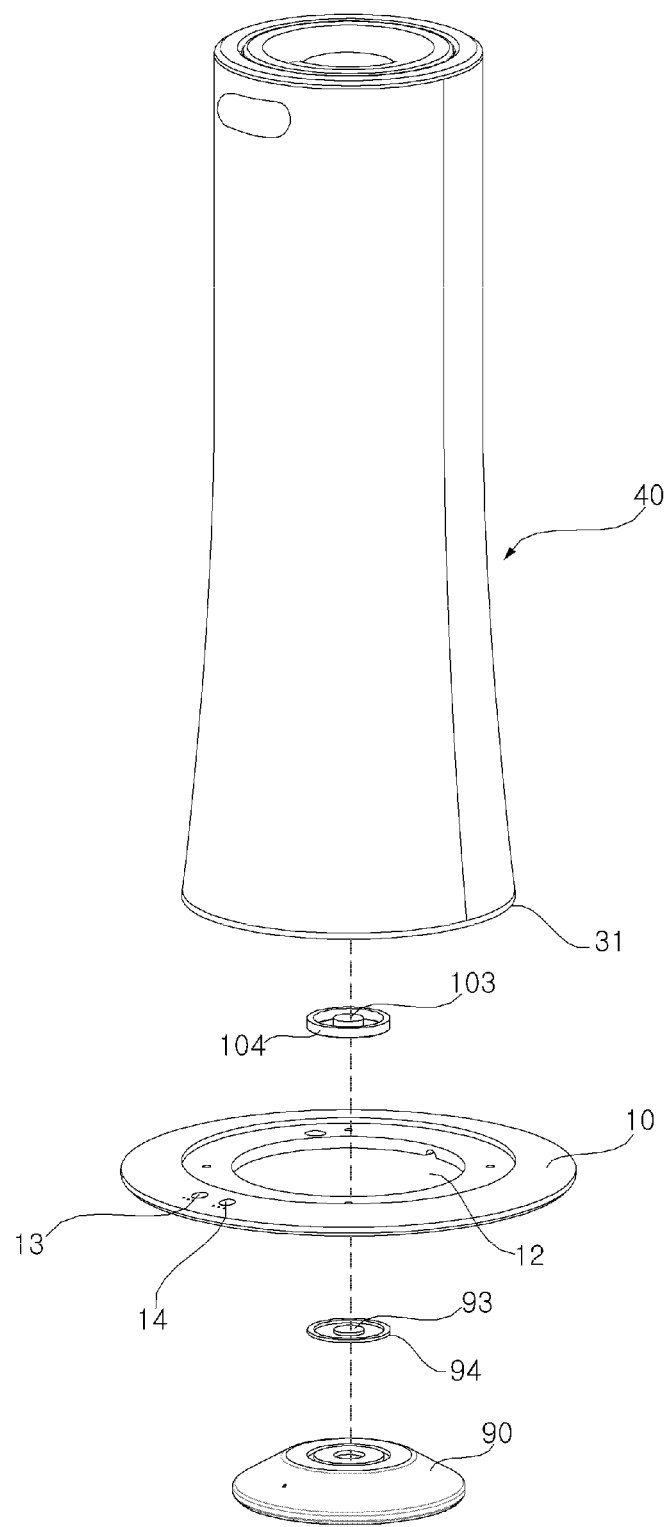
FIG. 9 is an exploded perspective view of a lower side of a dryer stand according to an embodiment of the present disclosure and a docking station.
Figure 10:
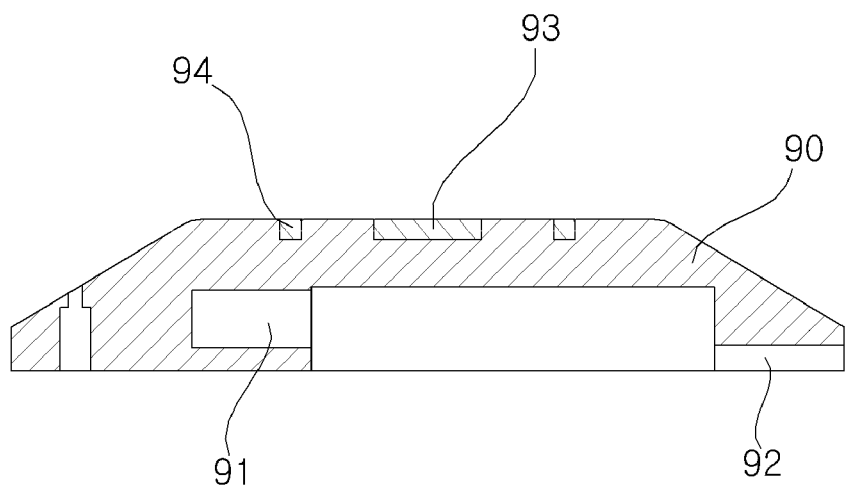
FIG. 10 is a cross-sectional view of the docking station shown in FIG. 9.

Referring to FIGS. 2, 9, and 10, a power supply means for applying external power to a dryer stand according to an embodiment of the present disclosure will be described.

The dryer stand is placed on the docking station 90 for changing. Referring to FIGS. 9 and 10, a recessed portion 92, through which an electric wire connected to an external power source passes, and a socket 91, into which a plug connected to one end of the electric wire is inserted, may be formed in a bottom surface of the docking station 90. In addition, a first external terminal 93 may be inserted into a central portion of the upper surface of the docking station 90, and a ring-shaped second external terminal 94 may be inserted at a periphery of the upper surface of the docking station 90.

When the stand is mounted to the docking station 90, the upper surface of the docking station 90 protrudes upward through a hollow portion 12 of the base 10 and thereby comes into contact with the bottom surface of the lower plate 31. In this case, a first inner terminal 103 electrically connected to the first external terminal 93 may be disposed at a center of the lower plate 31, and a second internal terminal 104 electrically connected to the second external terminal 94 may be disposed at a periphery of the first internal terminal 103. The second internal terminal 104 may have a ring shape.

The first internal terminal 103 and the first external terminal 93 electrically connected to each other are disposed at the center of the lower plate 31 and the docking station 90, and the second internal terminal 104 and the second external terminal 94 are formed in a ring shape. Accordingly, even when the dryer station and the docking station 90 are rotated separately, the aforementioned terminals may maintain the electrically connected state.

Figure 6:
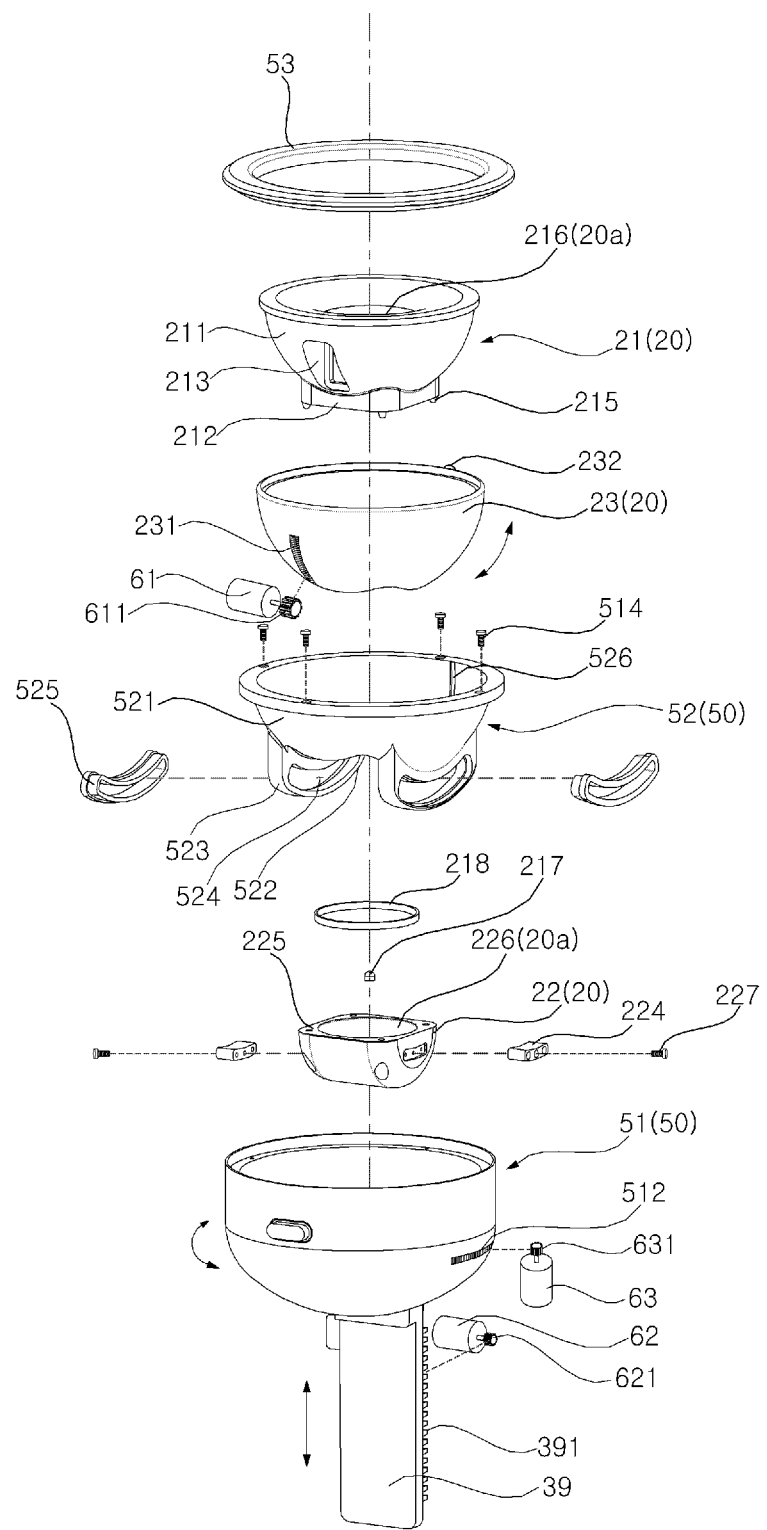
FIG. 6 is an upper exploded perspective view of a dryer stand according to an embodiment of the present disclosure.

In addition, referring to FIGS. 2, 6, and 7, a first contact terminal 217 and a second contact terminal 218, which can be electrically connected directly to the first external terminal 103 and the second external terminal 104 or which can be electrically connected to the battery 100, may be disposed inside the receptacle 20.

Additionally, a first subject contact terminal 2a and a second subject contact terminal 2b, which are electrically connected to the first contact terminal 217 and the second contact terminal 218, respectively, when inserted into the receptacle 20, may be disposed in the grip 2 of the dryer 1.

In the above, first contact terminal 217 and the first subject contact terminal 2a are disposed at the center of the bottom surface of the groove 20a of the receptacle 20a or at the center of the bottom surface of the grip 2 of the dryer, and the second contact terminal 218 and the second subject contact terminal 2b are formed in a ring shape. Accordingly, even when the grip 2 and the receptacle 20 of the dryer 1 are rotated relatively to each other, the contact terminals may maintain the electrical connected state. In the present disclosure, when the grip 2 is inserted into the groove 20a, the grip 2 is fixed to the groove 20a at a specific location by means of fixing means, such as a magnet M1, M2. Accordingly, the discharge direction of air for drying discharged through the outlet 3 of the dryer 1 can be changed by moving the receptacle 20.

The first and second contact terminals 217 and 218 may be electrically connected to the battery 100 and the first and second internal terminals 103 and 104, respectively, and a transfer switch 140 may be installed therebetween.

When the dryer 1 is mounted to the receptacle 20 and external power is applied from the docking station 90 to the first and second internal terminals 102 and 104, the controller 110 may manipulate the transfer switch 140 so that the first and second contact terminals 217 and 218 are electrically connected directly to the first and second internal terminals 103 and 104 and so that the first and second contact terminals 217 and 218 are electrically disconnected from the battery 100, thereby allowing the external power to be applied directly to the dryer 1 without passing through the battery 100.

Additionally, when the external power is not applied to the first and second internal terminals 103 and 104, the transfer switch 140 may be manipulated in the opposite way so that the first and second contact terminals 207 and 208 and the battery 100 are electrically connected to each other.

Figure 11:
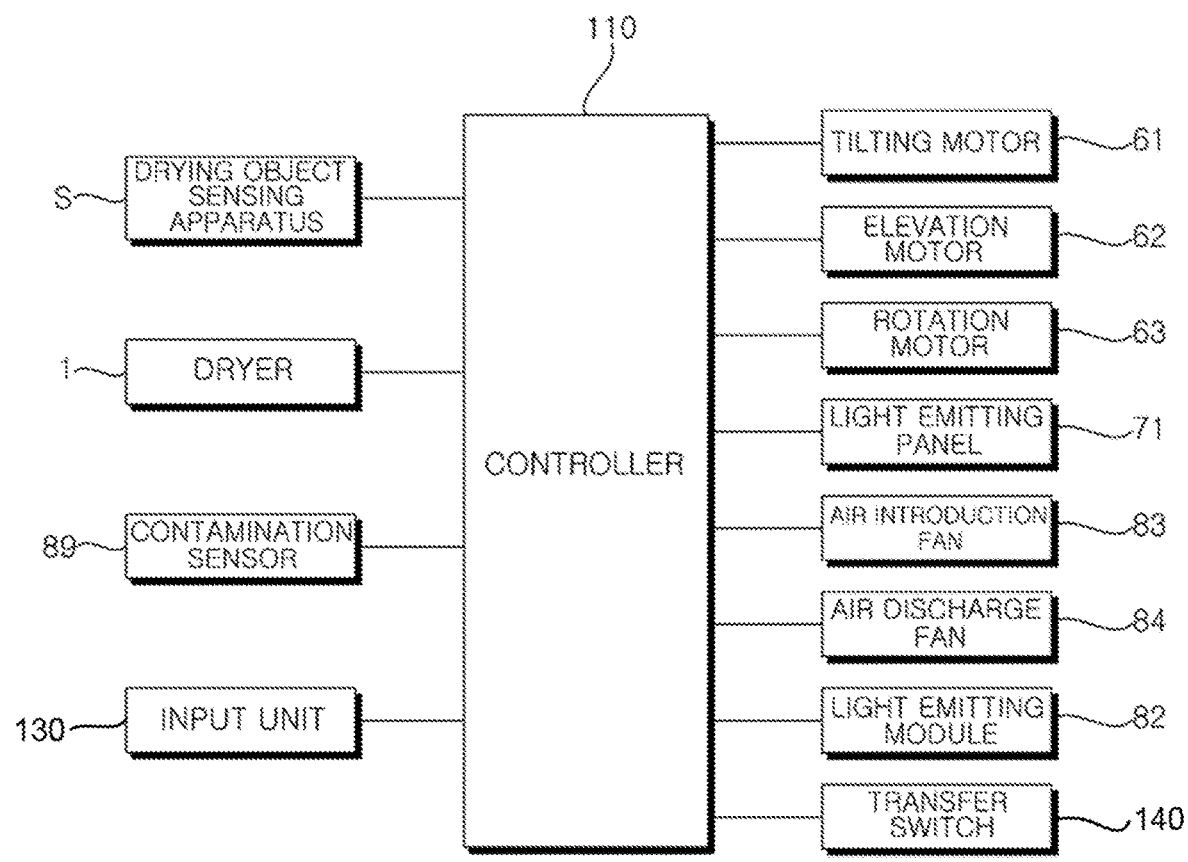
FIG. 11 is a block diagram showing a controller of a dryer stand according to an embodiment of the present disclosure.

Referring to FIG. 11, the controller 110 may adjust an air discharging direction of the dryer 1 mounted to the seating unit by controlling the motors 61, 62, and 63 based on information sensed by the drying object sensing apparatus S, may control a rotational speed of the blower fans 83 and 84 based on a sensed value of the contamination sensor 89, and may control turning on and off of the light emitting module 82 in accordance with an operation signal from an input unit 130 (or input assembly). The input unit 130 may be a switch (e.g., 13, 14 in FIG. 9) provided in the dryer stand or a smartphone connected to the dryer stand through known communication means.

When the sensed value of the contamination sensor 89 is greater, the controller 110 may control a speed of the blower fans 83 and 83 to be faster (e.g., to increase in relation to an increase in the sensed contamination value, and to decrease in relation to a decrease in the sensed contamination value). When the sensed value of the contamination sensor 89 is smaller than a preset reference contamination value, the controller 110 may operate the air introduction fan 83 and stop the air discharge fan 84. When the sensed value of the contamination sensor 89 is equal to or greater than the reference contamination value, the controller 110 may operate the air introduction fan 83 and the air discharge fan 84.

The preset reference contamination value may be set with reference to a concentration of harmful substance contained in the air. When the concentration of harmful substances corresponds to a degree not harmful to human health (for example, when a concentration of particulate matters is equal to or smaller than 30μg/m3) or a degree at which a user does not feel uncomfortable.

When the sensed value of the contamination sensor 89 is greater, the controller 110 may control the blower fans 83 and 83 to be rotated faster (e.g. to increase their rotational speed). When the sensed value of the contamination sensor 89 is smaller than the preset reference contamination value, the controller 110 may stop the air discharge fan 84. When the sensed value of the contamination sensor 89 is equal to or greater than the reference contamination value, the controller 110 may control the air discharge fan 84 to be rotated faster if the sensed value of the contamination sensor 89 is greater.

Figure 12:
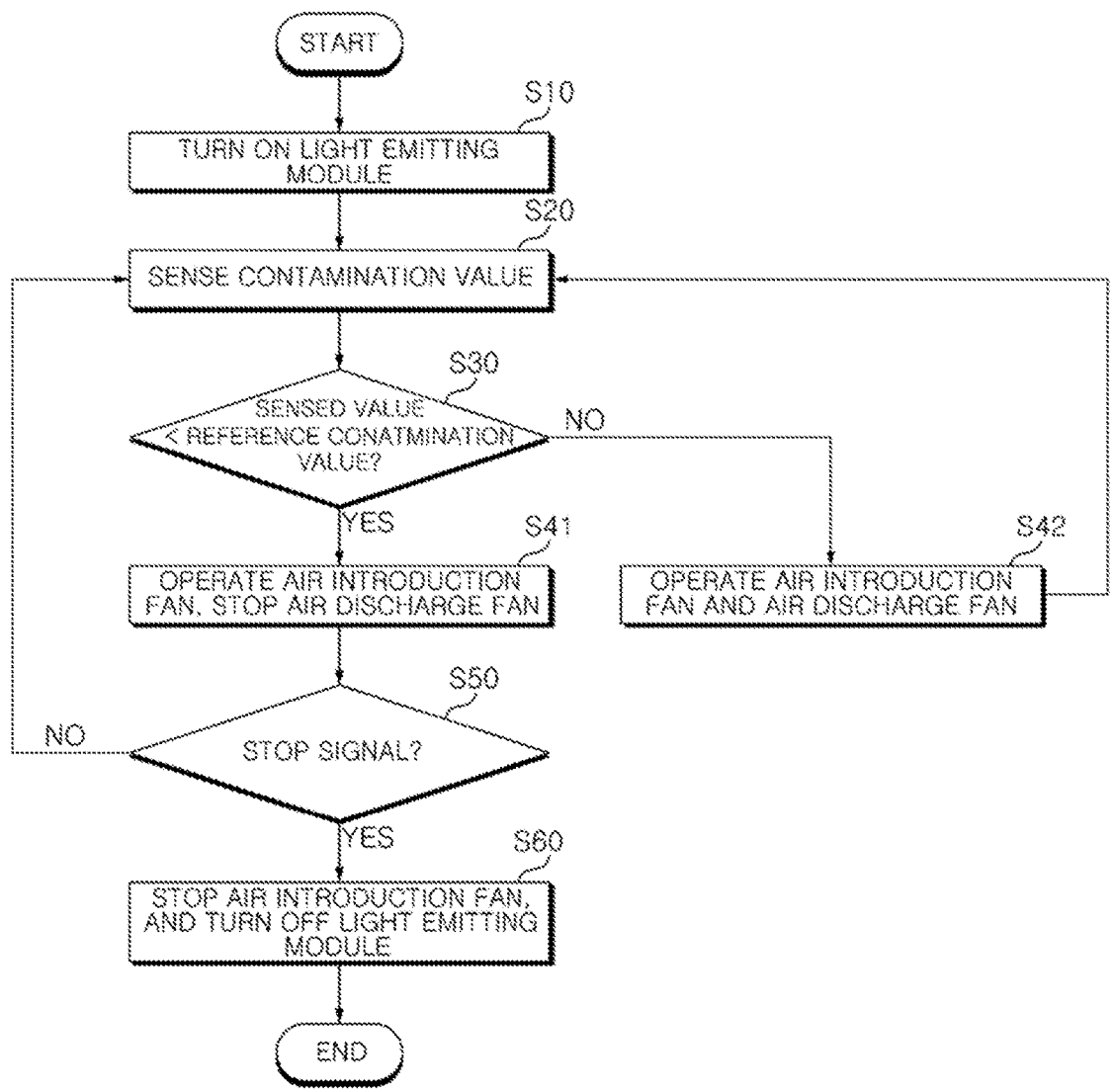
FIG. 12 is a flowchart of a control method of a dryer stand according to an embodiment of the present disclosure.

Referring to FIG. 12, a control method of a dryer stand according to an embodiment includes turning on the light emitting module 82, sensing a contamination value of air, determining whether a contamination sensed value is smaller than a preset reference contamination value, and operating the blower fan 83 and 84.

When an operation signal for the air purifier device 80 is input from an input unit 130, the controller 110 may turn on the light emitting module 82 to activate the photocatalyst filter 81 (S10) and may sense a contamination value using a contamination sensor (S20).

After sensing the contamination value, the controller 110 may determine whether the sensed contamination value is smaller than the preset reference contamination value (S30).

When a contamination sensed value is smaller than the reference contamination value, the controller 110 may operate the air introduction fan 83 and stop the air discharge fan 84 (S41). When it is determined that the contamination value sensed in S20 is smaller than the reference contamination value, the controller 110 may operate the air introduction fan 83 and stop the air discharge fan 84 (S41) and determine whether there is a stop signal (S50).

The stop signal may be input by a user through the input unit 130, may be generated after a preset period of time set in a timer expires, or may be set to be generated when a preset contamination value smaller than the reference contamination value is sensed.

When it is determined in the step S50 that there is no stop signal, the controller 110 may return to the step S20 to sense a contamination value again.

When it is determined in the step S50 that there is a stop signal, the controller 110 may stop the air introduction fan 83 and turn off the light emitting module 82 (S60). Accordingly, operation of the air purifying device 80 stops When the contamination sensed value is equal to or greater than the reference contamination value, the controller 110 operates the air introduction fan 83 and the air discharge fan 84 (S42). When it is determined in the step S20 that the sensed contamination value is equal to or greater than the reference contamination value, the controller 110 may operate the air introduction fan 83 and the air discharge fan 84 (S42) and then return to the step S20 to sense a contamination value again.

Although the above exemplary embodiments of the present disclosure have been described with reference to the accompanying drawings, the present disclosure should be construed in accordance with the spirit of the present disclosure. It should be understood that many variations and modifications of the basic inventive concept described herein will still fall within the spirit and scope of the present disclosure as defined in the appended claims and their equivalents.

What is claimed is:

1. A dryer stand, comprising:
   a seat comprising a groove configured to receive a dryer;
   a base spaced apart from the seat and positioned below the seat along a first axis;
   a side cover positioned between the base and the seat, the side cover having a through hole formed therein; and
   an air purifier disposed in an inner space defined by the side cover,
   wherein the air purifier comprises:
      at least one fan for generating an air flow; and
      a filter disposed in a flow path of air flowing by the at least one fan.

2. The dryer stand of claim 1, wherein the at least one fan comprises:
   an air introduction fan disposed in a lower portion of the inner space and directed upward along the first axis; and
   an air discharge fan disposed above the air introduction fan and directed toward the side cover,
   wherein the air introduction fan and the air discharge fan are provided above the base.

3. The dryer stand of claim 2, wherein the filter is disposed between the air introduction fan and the air discharge fan.

4. The dryer stand of claim 1, further comprising a stem supporting the seat,
   wherein the stem comprises a vertical plate extending in the inner space along the first axis and partitioning the inner space into a front part, which is located in a direction in which the dryer discharges drying air, and a rear part, which is opposite to the front part,
   wherein the front part and the rear part are disposed along a second axis, the second axis being perpendicular to the first axis, and
   wherein the air purifier is disposed in the rear part.

5. The dryer stand of claim 4, wherein the side cover comprises:
   a front cover forming an outer surface of the front part; and
   a rear cover forming an outer surface of the rear part, and
   wherein the through hole is formed in the rear cover.

6. The dryer stand of claim 4, wherein the stem further comprises a lower plate disposed above the base, and
   wherein the at least one fan comprises:
      an air introduction fan disposed on the lower plate and directed upward along the first axis; and
      an air discharge fan above the air introduction fan and directed toward the through hole.

7. The dryer stand of claim 4, wherein the stem further comprises:
   a lower plate disposed above the base; and
   a rear extension portion extending rearward along the second axis from an upper side of the vertical plate,
   wherein a rear side of the side cover comes into contact with a first side surface of the vertical plate, a second side surface of the vertical plate, an outer circumferential surface of the lower plate, and an outer circumferential surface of the rear extension portion, and
   wherein the first side surface of the vertical plate is opposite to the second side surface of the vertical plate.

8. The dryer stand of claim 4, wherein the at least one fan comprises an air introduction fan disposed below the rear part and directed upward along the first axis,
   wherein the stem further comprises a partition wall protruding rearward from the vertical plate along the second axis and partitioning the rear part along the first axis, and
   wherein a hole is formed in the partition wall and surrounds the air introduction fan.

9. The dryer stand of claim 8, wherein the stem further comprises:
   an upper supporting piece disposed above the partition wall and protruding rearward from the upper supporting piece along the second axis; and
   a lower supporting piece disposed behind the upper supporting piece and protruding upward from the partition wall along the first axis, and
   wherein the filter is detachably coupled to the upper supporting piece and the lower supporting piece.

10. The dryer stand of claim 1, wherein the filter comprises a photocatalyst filter to decompose substances by photochemical reaction, and
    wherein the air purifier further comprises a light emitter for activating the photocatalyst filter.

11. The dryer stand of claim 10, further comprising a vertical plate extending in the inner space in an upward-downward direction along the first axis and supporting the light emitter,
    wherein the photocatalyst filter extends in a downward direction substantially inclined from the vertical plate,
    wherein the downward direction is different than the upward-downward direction, and
    wherein a spacing between the photocatalyst filter and the light emitter increases in the downward direction.

12. The dryer stand of claim 1, further comprising:
    a contamination sensor to sense a contamination value of air introduced into the inner space; and
    a controller configured to:
       control operation of the air purifier, and
       control operation of the at least one fan based on a sensed value of the contamination sensor.

13. The dryer stand of claim 12, wherein the at least one fan comprises:
    a motor having a variable rotational speed; and
    a rotational blade rotated by the motor, and
    wherein the controller is further configured to control the rotational speed of the motor to increase in response to an increased sensed contamination value.

14. The dryer stand of claim 12, wherein the at least one fan comprises:
    an air introduction fan disposed in a lower portion of the inner space and directed upward along the first axis; and
    an air discharge fan disposed above the air introduction fan and directed toward the side cover, and wherein the controller is further configured to:
when the sensed contamination value of the contamination sensor is less than a preset reference contamination value, operate the air introduction fan and stop the air discharge fan, and
when the sensed contamination value of the contamination sensor is equal to or greater than the preset reference contamination value, operate the air introduction fan and the air discharge fan.

15. The dryer stand of claim 14, wherein the controller is further configured to control the air introduction fan to increase its rotational speed in response to an increased sensed contamination value, and
wherein the operation of the air discharge fan when the sensed contamination value of the contamination sensor is equal to or greater than the preset reference contamination value comprises controlling the air discharge fan to increase its rotational speed in response to the increased sensed contamination value.

16. The dryer stand of claim 12, wherein the at least one fan comprises an air introduction fan disposed in a lower portion of the inner space and directed upward along the first axis, and
wherein the contamination sensor is disposed in the lower portion of the inner space.

17. A method of controlling a dryer stand on which a dryer is placed, the dryer stand including a seat comprising a groove configured to receive the dryer, a light emitter, a photocatalyst filter, an air introduction fan and an air discharge fan, the method comprising:

turning on the light emitter for activating the photocatalyst filter;
operating the air introduction fan to introduce air from outside the dryer stand to the photocatalyst filter;
sensing a contamination value of air introduced from the outside of the dryer stand by the air introduction fan; and
based on the sensed contamination value, controlling the air introduction fan and controlling the air discharge fan.

18. The method of claim 17, wherein the method further comprises, in response to the sensed contamination value being greater than or equal to a preset reference contamination value, controlling the air discharge fan to operate and controlling the air introduction fan to operate, and
wherein the operating of the air discharge fan includes discharging air from the photocatalyst filter and to the outside of the dryer stand.

19. The method of claim 17, wherein the method further comprises, in response to the sensed contamination value being smaller than a preset reference contamination value, controlling the air introduction fan to operate and controlling the air discharge fan to stop operating.

20. The method of claim 17, wherein the air discharge fan is located above the photocatalyst filter and faces a first direction,
wherein the air introduction fan faces a second direction toward the photocatalyst filter, and
wherein the first direction is substantially perpendicular to the second direction.

* * * * *